United States Patent [19]

Wright, Jr. et al.

[11] 4,347,248

[45] Aug. 31, 1982

[54] 2,3-DISUBSTITUTED-THIAZOLO[3,2-A]PYRIMIDINES

[75] Inventors: William B. Wright, Jr., Woodcliff Lake; Andrew S. Tomcufcik, Old Tappan, both of N.J.; Joseph W. Marsico, Jr., Pearl River, N.Y.

[73] Assignee: American Cyanamid Company, Stamford, Conn.

[21] Appl. No.: 246,347

[22] Filed: Mar. 23, 1981

[51] Int. Cl.$^3$ .................. C07D 513/04; A61K 31/38
[52] U.S. Cl. .................................. 424/251; 544/278; 260/245.5; 424/244
[58] Field of Search ................... 544/278; 424/251

[56] References Cited

U.S. PATENT DOCUMENTS

| 3,671,526 | 6/1972 | Manning | 544/278 |
| 3,686,173 | 8/1972 | Houlihan | 424/251 |
| 4,110,451 | 8/1978 | Moser et al. | 424/251 |

OTHER PUBLICATIONS

Houlihan, W. et al., Chemical Abstract, 72:111502w.

Primary Examiner—Anton H. Sutto
Assistant Examiner—Sharon A. Gibson
Attorney, Agent, or Firm—Edward A. Conroy, Jr.

[57] ABSTRACT

This disclosure describes 2,3-disubstituted-thiazolo[3,2-a]pyrimidines which are useful as diuretic agents.

7 Claims, No Drawings

2,3-DISUBSTITUTED-THIAZOLO[3,2-A]PYRIMIDINES

BRIEF SUMMARY OF THE INVENTION

This invention relates to new organic compounds and, more particularly, is concerned with novel 2,3-disubstituted-thiazolo[3,2-a][1,3]diazacyclenes which may be represented by the following structural formula:

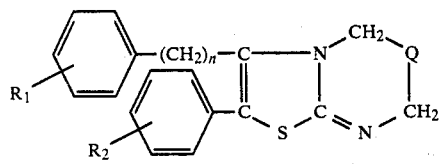

(I)

wherein $R_1$ is hydrogen, fluoro, chloro, bromo, alkyl having up to 3 carbon atoms or dimethylamino; $R_2$ is hydrogen, fluoro, chloro, bromo or alkyl having up to 3 carbon atoms; n is zero, one or two; and Q is a divalent moiety of the formulae:

—$CH_2$—

—$CH_2CH_2$— or —$CH_2CH_2CH_2$—; as well as the pharmaceutically acceptable acid-addition salts thereof. The invention is also concerned with pharmaceutical compositions comprising these new compounds as well as methods for inducing diuresis employing these new compounds and, further, to methods for their preparation.

DETAILED DESCRIPTION OF THE INVENTION

The novel free bases of the present invention are obtainable as either white to light tan crystalline materials having characteristic melting points or as oils having characteristic absorption spectra. The free bases are, in general, relatively insoluble in water but soluble in most organic solvents such as lower alkanols, benzene, acetone, chloroform, etc. The organic bases of this invention form acid-addition salts with a variety of pharmacologically acceptable organic and inorganic salt-forming reagents. Thus, acid-addition salts, formed by admixture of the organic free base with an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free bases are equivalent to their acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

Some of the novel compounds of the present invention may be readily prepared in accordance with the following reaction scheme:

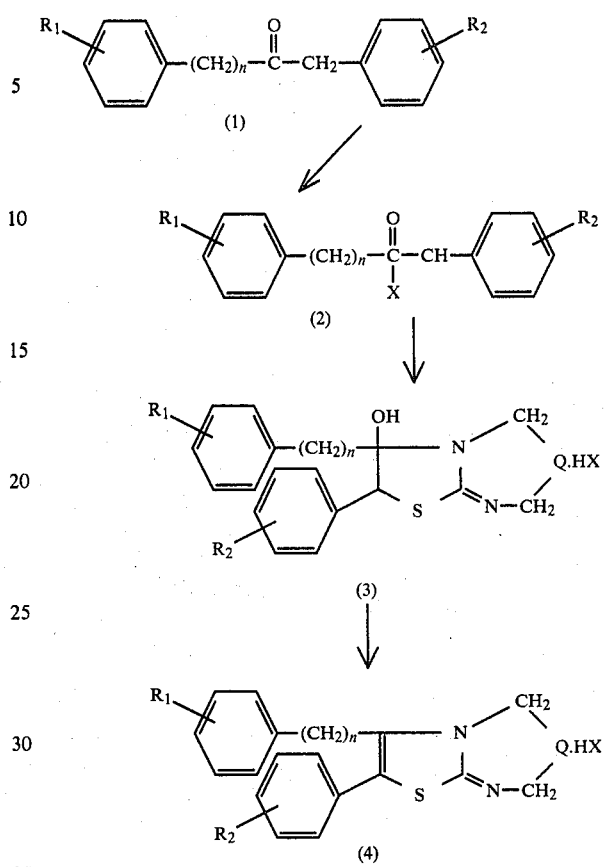

wherein X is chloro or bromo, n is one or two, and $R_1$, $R_2$ and Q are as hereinbefore defined. In accordance with the above reaction scheme, an appropriately substituted 1,3-diphenyl-2-propanone or 1,4-diphenyl-2-butanone (1) is halogenated to produce the corresponding 1-halo-2-alkanones (2). Treatment of (2) with tetrahydropyrimidine-2(1H)-thione, tetrahydro-5,5-dimethylpyrimidine-2(1H)-thione, hexahydro-1,3-diazepin-2(2H)-thione or hexahydro-1,3-diazocin-2(1H)-thione provides the corresponding 2,3-disubstituted-thiazolo[3,2-a][1,3]diazacyclan-3-ol (3). Heating the diazacyclan ol (3) above its decomposition point, usually 160°-220° C., for from about 5 to about 30 minutes provides the dehydrated product (4).

Other of the novel compounds of the present invention may be readily prepared in accordance with the following reaction scheme:

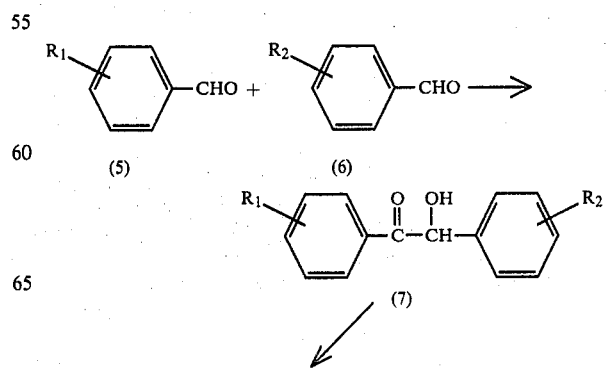

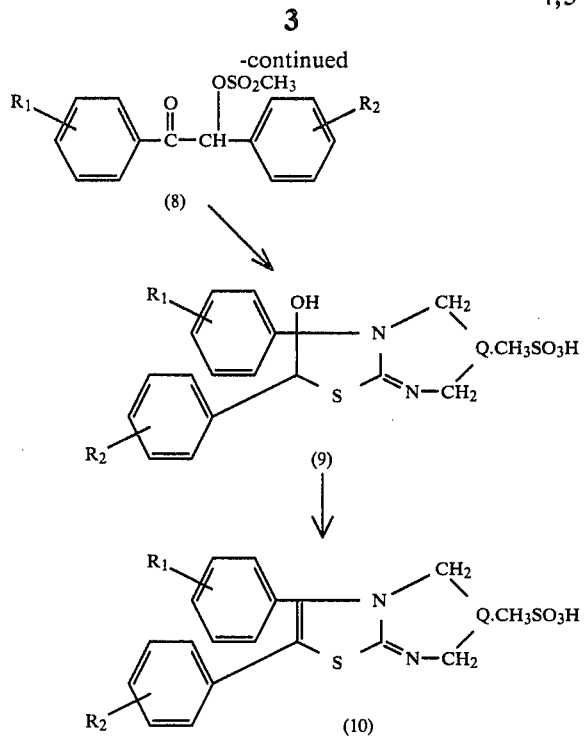

wherein $R_1$, $R_2$ and Q are as hereinbefore defined. In accordance with the above reaction scheme, the benzoin derivatives (7) are prepared by the interaction of the benzaldehydes (5) and (6) in the presence of KCN in aqueous ethanol at the reflux temperature for several hours. The benzoin (7) is then suspended or dissolved in toluene containing a small portion of triethylamine and reacted with methanesulfonyl chloride for several hours, followed by dilution with water, giving the methane sulfonate derivatives (8) which are then reacted with a cyclic urea as described in the first reaction scheme giving the compounds (9). In an alternative procedure, the diazacyclanols (3) or (9) may be dissolved in a solvent such as ethanol, butanol or dioxane and heated until dehydration is complete. Addition of an acid such as hydrochloric or hydrobromic promotes the reaction.

The 1,3-diphenyl-2-propanone or 1,4-diphenyl-2-butanone starting materials may be prepared by well known literature procedures such as R. D. Haworth, C. R. Marin and G. Sheldrick, J. Chem. Soc., 1423, 1934; J. Kenner and F. Morton, J. Chem. Soc., 679, 1934; E. C. S. Jones and J. Kenner, J. Chem. Soc., 1842, 1931; R. C. Elderfield and K. L. Burgess, J. A. C. S. 82, 1975, (1960); J. A. King and F. H. McMillan, J. A. C. S. 73, 4911–4915, (1951).

In general terms, the halogenation step of (1) to (2) may be carried out at 0°–50° C., for 5–60 minutes in solvents such as methylene chloride, chloroform, toluene or acetic acid. The cyclization step leading to derivative (3) may be carried out at 20°–80° C. for from one to 72 hours in solvents such as acetone, methylethyl ketone, benzene or methylene chloride.

A preferred embodiment of the present invention may be represented by structural formula (I) but wherein $R_1$ is hydrogen, fluoro, chloro, bromo, methyl or methoxy; $R_2$ is hydrogen, fluoro, chloro, bromo or methyl; n is zero or one; and Q is as defined for structural formula (I); as well as the pharmacologically acceptable acid-addition salts thereof.

The new compounds of the present invention posses diuretic activity in warm-blooded animals as established when tested by the method of P. S. Chan and D. Poorvin, Clinical and Experimental Hypertension, 1 (6), 817–830 (1979), Sequential Method for Combined Screening Antihypertensive and Diuretic Agents in the Same Spontaneously Hypertensive Rat.

Basically this test uses male, 8 week old, spontaneously hypertensive rats of the Okamoto strain weighing about 300 g. One rat is dosed by gavage with the test compound at 100 mg./kg. of body weight with 0.9% sodium chloride loading at 25 ml./kg. of body weight at zero hour. The test compound is suspended in 2% preboiled starch at 50 mg./ml. The rat is placed in a metabolism cage and the 0–5 hour urine is collected. The urinary sodium and potassium content are determined by the Technicon Autoanalyzer; method N-20 for sodium and potassium. Based on the data obtained and using the three-stage "sequential probability ratio test", statistical method, the criteria for determining if a test compound is considered active are as follows:

Test I: If the urinary sodium is $\geq 1.21$ mEq the compound is active. If the urinary sodium is between 1.21–0.93, a second rat is tested.

Test II: If the average urinary sodium of the two rats $>1.16$ mEq the compound is considered active. If the average urinary sodium is between 1.16–1.01 a third rat is tested.

Test III: If the average urinary sodium is $\geq 1.10$ the compound is active.

The results of these tests on representative compounds of the present invention appear in Table I.

TABLE I

| Compound | Urinary Values in mEq/5 Hours | | |
|---|---|---|---|
| | Volume (ml.) | Na+ | K+ |
| 3-Benzyl-6,7-dihydro-6,6-dimethyl-2-phenyl-5H-thiazolo[3,2-a]pyrimidine hydrobromide | 13.5 | 1.56 | 0.59 |
| 3-Benzyl-6,7,8,9-tetrahydro-2-phenyl-5H-thiazolo[3,2-a][1,3]diazocine hydrobromide | 10.0 | 1.75 | 0.57 |
| 3-p-Fluorobenzyl-2-(p-fluorophenyl)-6,7-dihydro-5H-thiazolo[3,2-a]pyrimidine hydrobromide | 11.5 | 1.48 | 0.67 |
| 3-p-Fluorobenzyl-2-(p-fluorophenyl)-6,7,8,9-tetrahydro-5H-thiazolo[3,2-a][1,3]diazocine hydrobromide | 9.8 | 1.54 | 0.61 |
| 2-o-Fluorophenyl-6,7-dihydro-3-(p-methoxyphenyl)-5H-thiazolo[3,2-a]pyrimidine hydrochloride | 12.8 | 1.61 | 0.71 |
| 6,7-Dihydro-3-p-methoxyphenyl-6,6-dimethyl-2-phenyl-5H-thiazolo[3,2-a]pyrimidine hydrochloride | 18.8 | 2.28 | 0.79 |

The compounds of the present invention have thus been shown to be valuable diuretic agents of low toxicity when administered orally. The amount of a single dose or of a daily dose will vary but should be such as to give a proportionate dosate of from about 5 mg. to about 100 mg. per day for a subject of about 70 kg. body weight. The dosage regimen may be adjusted to provide the optimum therapeutic response, for example, doses of 1.0–25 mg. may be administered on a four times per day regimen, or the dose may be proportionately increased as indicated by the exigencies of the therapeutic situation.

The compounds of the present invention may be administered as active components of compositions in dosage unit form such as tablets, pills, capsules, powders, granules, oral solutions or suspensions and the like. For preparing solid compositions such as tablets, the active compound is mixed with conventional tableting ingredients such as starch, lactose, sucrose, sorbitol, talc, stearic acid, magnesium stearate, dicalcium phosphate, gums and functionally similar materials as pharmaceutical diluents or carriers. The tablets or pills can be laminated or otherwise compounded to provide a dosage form affording the advantage of prolonged or delayed action, or predetermined successive action of the enclosed medication. For example, the tablet or pill can comprise an inner dosage and an outer dosage component, the latter being in the form of an envelop over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolymer together with known materials contributing to the enteric properties of the coating.

The liquid forms in which the compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The term dosage unit form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use.

The invention will be described in greater detail in conjunction with the following specific examples.

EXAMPLE 1

3-Benzyl-2,3,6,7-tetrahydro-2-phenyl-5H-thiazolo-[3,2-a]pyrimidin-3-ol hydrobromide A solution of 2.1 g. of 1,3-diphenyl-2-propanone in 20 ml. of methylene chloride is stirred and a solution of 0.45 ml. of bromine in 10 ml. of methylene chloride is added dropwise over a 15 minute period. The reaction mixture is concentrated to remove the solvent and the residue is dissolved in 20 ml. of acetone. This solution is added to a boiling mixture of 1.04 g. of 3,4,5,6-tetrahydro-2-pyrimidine thione in 80 ml. of acetone. The reaction mixture is allowed to stand at room temperature for 24 hours and the precipitate is collected by filtration and recrystallized from ethanol, giving the title product, m.p. 192°–194° C. (dec.).

When the procedure of Example 1 is carried out using 1,3-diphenyl-2-propanone or other appropriate 1,3-bis-(aryl)-2-propanones of 1,4-bis-(aryl)-2-butanones, which are prepared by literature reference procedures, and 3,4,5,6-tetrahydro-2-pyrimidine thione or other appropriate cyclic ureas, the resulting brominated intermediates of Examples 2–18 are obtained (listed in tabular form).

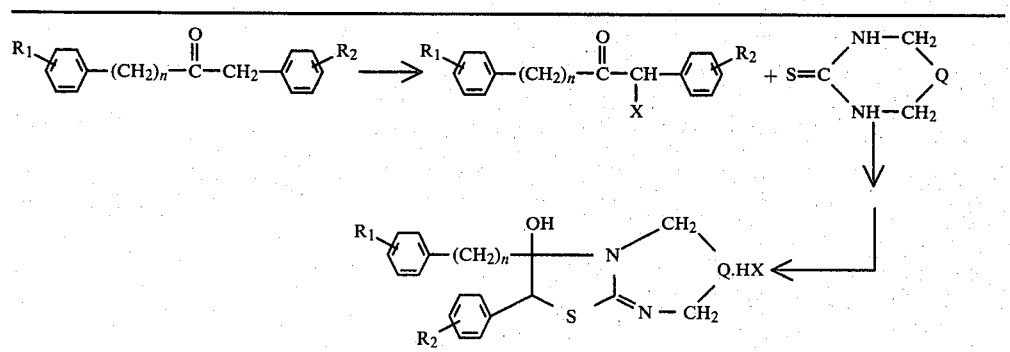

| Ex. | $R_1$ | $R_2$ | n | Q | X | Product | m.p. °C. |
|---|---|---|---|---|---|---|---|
| 2 | H | H | 1 | $(CH_2)_2$ | Br | 3-Benzyl-2,3,5,6,7,8-hexahydro-2-phenylthiazolo[3,2-a]-[1,3]diazepin-3-ol hydrobromide | 165–167 |
| 3 | H | H | 1 | $C(CH_3)_2$ | Br | 3-Benzyl-2,3,6,7-tetrahydro-6,6-dimethyl-2-phenyl-5H-thiazolo[3,2-a]pyrimidin-3-ol hydrobromide | 153–155 |
| 4 | H | H | 1 | $(CH_2)_3$ | Br | 3-Benzyl-2,3,6,7,8,9-hexahydro-2-phenyl-5H-thiazolo-[3,2-a][1,3]diazocin-3-ol hydrobromide | 192–194 |
| 5 | p-F | p-F | 1 | $CH_2$ | Br | 3-p-Fluorobenzyl-2-(p-fluorophenyl)-2,3,6,7-tetrahydro-5H-thiazolo[3,2-a]pyrimidin-3-ol hydrobromide | 193–195 |
| 6 | p-F | p-F | 1 | $(CH_2)_2$ | Br | 3-p-Fluorobenzyl-2-(p-fluorophenyl)-2,3,5,6,7,8-hexahydrothiazolo[3,2-a][1,3]diazepin-3-ol hydrobromide | 162–164 |
| 7 | p-F | p-F | 1 | $(CH_2)_3$ | Br | 3-p-Fluorobenzyl-2-(p-fluorophenyl)-2,3,6,7,8,9-hexahydro-5H-thiazolo[3,2-a][1,3]diazocin-3-ol hydrobromide | 205–207 |
| 8 | m-Cl | m-Cl | 1 | $(CH_2)_2$ | Br | 3-m-Chlorobenzyl-2-(m-chlorophenyl)-2,3,5,6,7,8-hexa- | 203–205 |

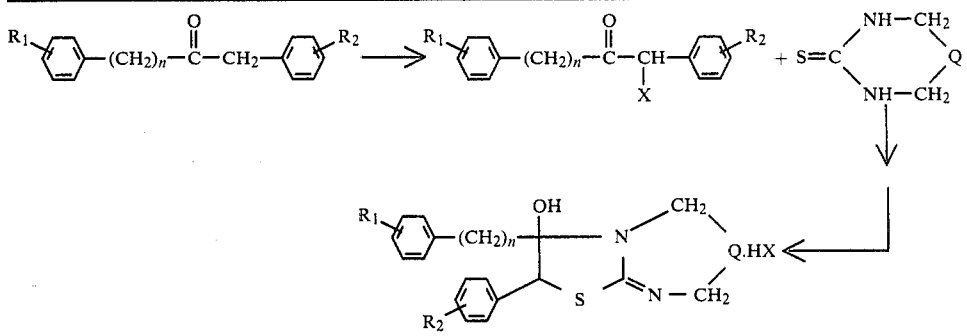

| Ex. | R₁ | R₂ | n | Q | X | Product | m.p. °C. |
|---|---|---|---|---|---|---|---|
| 9 | m-Cl | m-Cl | 1 | C(CH₃)₂ | Br | 3-m-Chlorobenzyl-2-(m-chlorophenyl)-2,3,6,7-tetrahydro-6,6-dimethyl-5H-thiazolo[3,2-a]pyrimidin-3-ol hydrobromide | 202–204 |
| 10 | p-Cl | p-Cl | 1 | (CH₂)₃ | Br | 3-p-Chlorobenzyl-2-(p-chlorophenyl)-2,3,6,7,8,9-hexahydro-5H-thiazolo[3,2-a][1,3]diazocin-3-ol hydrobromide | 206–208 |
| 11 | p-Br | p-Br | 1 | C(CH₃)₂ | Br | 3-p-Bromobenzyl-2-(p-bromophenyl)-2,3,6,7-tetrahydro-6,6-dimethyl-5H-thiazolo[3,2-a]pyrimidin-3-ol hydrobromide | 186–187 |
| 12 | m-F | m-F | 1 | (CH₂)₂ | Br | 3-m-Fluorobenzyl-2-(m-fluorophenyl)-2,3,5,6,7,8-hexahydrothiazolo[3,2-a][1,3]diazepin-3-ol hydrobromide | 176–178 |
| 13 | m-F | m-F | 1 | (CH₂)₃ | Br | 3-m-Fluorobenzyl-2-(m-fluorophenyl)-2,3,6,7,8,9-hexahydro-5H-thiazolo[3,2-a][1,3]diazocin-3-ol hydrobromide | 198–200 |
| 14 | p-CH₃ | p-CH₃ | 1 | C(CH₃)₂ | Br | 2,3,6,7-Tetrahydro-6,6-dimethyl-3-p-methylbenzyl-2-p-tolyl-5H-thiazolo[3,2-a]pyrimidin-3-ol hydrobromide | 163–165 |
| 15 | p-CH₃ | p-CH₃ | 1 | (CH₃)₃ | Br | 2,3,6,7,8,9-Hexahydro-3-p-methylbenzyl-2-p-tolyl-5H-thiazolo[3,2-a][1,3]diazocin-3-ol hydrobromide | 168–170 |
| 16 | m-CH₃ | m-CH₃ | 1 | (CH₂)₂ | Br | 2,3,5,6,7,8-Hexahydro-3-m-methylbenzyl-2-m-tolylthiazolo[3,2-a][1,3]diazepin-3-ol hydrobromide | 187–189 |
| 17 | m-CH₃ | m-CH₃ | 1 | C(CH₃)₂ | Br | 2,3,6,7-Tetrahydro-6,6-dimethyl-3-m-methylbenzyl-2-m-tolyl-5H-thiazolo[3,2-a]pyrimidin-3-ol hydrobromide | 185–187 |
| 18 | p-F | p-F | 1 | C(CH₃)₂ | Br | 3-p-Fluorobenzyl-2-(p-fluorophenyl)-2,3,6,7-tetrahydro-6,6-dimethyl-5H-thiazolo[3,2-a]pyrimidin-3-ol hydrobromide | 181–183 |

EXAMPLE 19

2,3,6,7-Tetrahydro-3-(p-methoxyphenyl)-6,6-dimethyl-2-phenyl-5H-thiazolo[3,2-a]pyrimidin-3-ol hydrochloride A mixture of 24.4 ml. of anisaldehyde, 20.2 ml. of benzaldehyde, 8 g. of potassium cyanide and 200 ml. of 65% ethanol is refluxed for 1½ hours, diluted with 60 ml. of water and placed in a freezer for 2 hours. The resulting solid is crystallized from 50% ethanol giving p-methoxybenzoin as white crystals.

A mixture of 13.3 g. of p-methoxybenzoin, 15.3 ml. of triethylamine and 100 ml. of toluene is stirred while a mixture of 4.7 ml. of methane sulfonyl chloride in 100 ml. of toluene is added. The mixture is stirred overnight, water is added and the organic layer is concentrated to an oil which is crystallized from ether, giving 11.0 g. of the methane sulfonate ester of p-methoxybenzoin.

A mixture of 3.20 g. of the above methane sulfonate ester and 1.42 g. of 2,3,6,7-tetrahydro-5,5-dimethyl-2(1H)-pyrimidine thione in 100 ml. of acetone is warmed until solution is complete, filtered and then cooled, The solution is concentrated to a low volume, alcoholic hydrochloric acid is added and the mixture is refrigerated, then concentrated and acetone is added, giving, after further refrigeration 2.0 g. of the desired product as white crystals, m.p. 180°–182° C.

EXAMPLE 20

2-(o-Fluorophenyl)-2,3,6,7-tetrahydro-3-(p-methoxyphenyl)-5H-thiazolo[3,2-a]pyrimidin-3-ol hydrochloride A mixture of 13.6 g. of anisaldehyde, 10.5 ml. of o-fluorobenzaldehyde, 8 g. of potassium cyanide and 100 ml. of 65% ethanol is stored in a refrigerator for 2 hours, then 30 ml. of water are added and refrigeration is continued. The precipitate is crystallized from 90% ethanol giving 6.7 g. of o-fluoro-p-methoxybenzoin.

A mixture of 5.2 g. of the above benzoin derivative 5.6 ml. of triethylamine, 1.71 ml. of methane sulfonyl chloride and 80 ml. of toluene are reacted as described in Example 19, giving the methane sulfonate ester as an oil which is then reacted with 0.93 g. of 3,4,5,6-tetrahydro-2-pyrimidine thione as described in Example 19, giving 2.2 g. of the desired product as white crystals, m.p. 191°–193° C.

EXAMPLE 21

3-p-Fluorobenzyl-2-(p-fluorophenyl)-6,7-dihydro-5H-thiazolo[3,2-a]pyrimidine hydrobromide A test tube containing 1.4 g. of 3-p-fluorobenzyl-2-(p-fluorophenyl)-2,3,6,7-tetrahydro-5H-thiazolo[3,2-a]pyrimidin-3-ol hydrobromide (Ex. 5) is immersed in an oil bath at 200° C. for 15 minutes. The test tube is removed, acetone is added and the crystalline solid is recovered by filtration, giving the desired product, m.p. 248°–250° C.

When the appropriate 2,3,6,7-tetrahydro-5H-thiazolo-[3,2-a]pyrimidin-3-ol salt is reacted by a procedure similar to Example 21, the products of Examples 22–28 (listed in tabular form) are derived.

A 3.68 g. portion of the above ester, 1.17 g. of hexahydro-2H-1,3-diazepin-2-thione and 130 ml. of acetone are reacted as described in Example 19, giving 2.9 g. of the desired product, m.p. 184°–186° C.

| Ex. | Starting Material Example | $R_1$ | $R_2$ | n | Q | X | Product | Reaction Conditions Minutes | °C. | m.p. °C. |
|---|---|---|---|---|---|---|---|---|---|---|
| 22 | 3 | H | H | 1 | $C(CH_3)_2$ | Br | 3-Benzyl-6,7-dihydro-6,6-dimethyl-2-phenyl-5H-thiazolo[3,2-a]pyrimidine hydrobromide | 25 | 190 | 173–175 |
| 23 | 19 | p-$CH_3O$ | H | 0 | $C(CH_3)_2$ | Cl | 6,7-Dihydro-3-p-methoxyphenyl-6,6-dimethyl-2-phenyl-5H-thiazolo[3,2-a]pyrimidine hydrochloride | 25 | 190–205 | 270–272 |
| 24 | 20 | p-$CH_3O$ | o-F | 0 | $CH_2$ | Cl | 2-o-Fluorophenyl-6,7-dihydro-3-(p-methoxyphenyl)-5H-thiazolo[3,2-a]pyrimidine hydrochloride | 20 | 200 | 225–228 |
| 25 | 18 | p-F | p-F | 1 | $C(CH_3)_2$ | Br | 3-p-Fluorophenyl-2-p-fluorophenyl-6,7-dihydro-6,6-dimethyl-5H-thiazolo-[3,2-a]pyrimidine hydrobromide | 20 | 200 | 191–193 |
| 26 | 9 | m-Cl | m-Cl | 1 | $C(CH_3)_2$ | Br | 3-m-Chlorophenyl-2-m-chlorophenyl-6,7-dihydro-6,6-dimethyl-5H-thiazolo-[3,2-a]pyrimidine hydrobromide | 20 | 200 | |
| 27 | 14 | p-$CH_3$ | p-$CH_3$ | 1 | $C(CH_3)_2$ | Br | 6,7-Dihydro-6,6-dimethyl-3-p-methylbenzyl-2-p-tolyl-5H-thiazolo[3,2-a]pyrimidine hydrobromide | 20 | 190 | 212–214 |

EXAMPLE 28

2-(m-Chlorophenyl)-2,3,5,6,7,8-hexahydro-3-(p-dimethylaminophenyl)-thiazolo[3,2-a][1,3]diazepin-3-ol methanesulfonate A mixture of 11.2 g. of p-dimethylaminobenzaldhyde, 13.5 g. of m-chlorobenzaldehyde, 4.5 g. of potassium cyanide and 70 ml of 65% ethanol is reacted as described in Example 19, giving 6.4 g. of 3′-chloro-4-dimethylaminobenzoin.

A 4.35 g. portion of the above benzoin derivative, 4.2 ml. of triethylamine, 1.25 ml. of methane sulfonyl chloride and 60 ml. of toluene are reacted as described in Example 19 giving 4.2 g. of 3′-chloro-4-dimethylaminobenzoin, methane sulfonate ester.

EXAMPLE 29

3-Benzyl-5,6,7,8-tetrahydro-2-phenylthiazolo[3,2-a][1,3]-diazepine hydrobromide

An Erlenmyer flask containing 3.0 g. of 3-benzyl-2,3,5,6,7,8-hexahydro-2-phenylthiazolo[3,2-a][1,3]diazepin-3-ol hydrobromide (Ex. 2) is immersed in an oil bath at 170° C. and left for 25 minutes while the temperature is gradually raised to 185° C. The flask is removed and the reaction mixture is triturated with acetone and filtered giving the desired product, m.p. 205°–208° C.

When the appropriate 2,3,5,6,7,8-hexahydro-thiazolo[3,2-a][1,3diazepin-3-ol salt is reacted by a procedure similar to Example 30, the products of Examples 31–34 (listed in tabular form) are derived.

| Ex. | Starting Material Example | $R_1$ | $R_2$ | n | Q | X | Product | Reaction Conditions Minutes | °C. | m.p. °C. |
|---|---|---|---|---|---|---|---|---|---|---|
| 30 | 6 | p-F | p-F | 1 | $(CH_2)_2$ | Br | 3-p-Fluorobenzyl-2-(p-fluorophenyl)-5,6,7,8-tetrahydro-thiazolo[3,2-a][1,3]-diazepine hydro- | 20 | 185–190 | 197–199 |

-continued

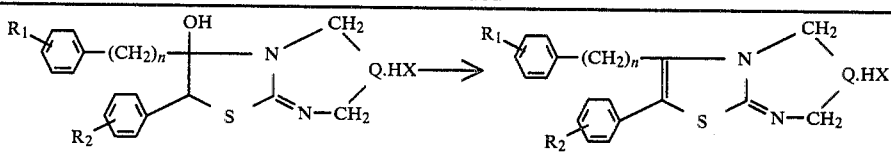

| Ex. | Starting Material Example | R₁ | R₂ | n | Q | X | Product | Reaction Conditions Minutes | °C. | m.p. °C. |
|---|---|---|---|---|---|---|---|---|---|---|
| 31 | 16 | m-CH₃ | m-CH₃ | 1 | (CH₂)₂ | Br | bromide 5,6,7,8-Tetrahydro-3-m-methylbenzyl-2-m-tolylthiazolo-[3,2-a][1,3]diazepine hydrobromide | 15 | 195–200 | 169–171 |
| 32 | 8 | m-Cl | m-Cl | 1 | (CH₂)₂ | Br | 3-m-Chlorobenzyl-2-(m-chlorophenyl)-5,6,7,8-tetrahydro-thiazolo[3,2-a][1,3]-diazepine hydrobromide | 20 | 190 | 203–205 |
| 33 | 29 | p-N(CH₃)₂ | m-Cl | 0 | (CH₂)₂ | CH₃SO₃ | 2-m-Chlorophenyl-5,6,7,8-tetrahydro-3-(p-dimethylamino-phenyl)thiazolo[3,2-a][1,3]diazepine methanesulfonate | 15 | 200 | 204–260 |

EXAMPLE 34

3-p-Fluorobenzyl-2-(p-fluorophenyl)-6,7,8,9-tetrahydro-5H-thiazolo[3,2-a][1,3]diazocine hydrobromide A test tube containing 1.5 g. of 3-p-fluorobenzyl-2-(p-fluorophenyl)-2,3,6,7,8,9-hexahydro-5H-thiazolo-[3,2-a][1,3]diazocin-3-ol hydrobromide (Ex. 7) is immersed in an oil bath at 205° C. and left for 10 minutes while the temperature is raised to 212° C. The tube is removed, 10 ml. of acetone are added and the mixture is cooled, giving 1.1 g. of the desired product as pale yellow crystals, which, after recrystallization from ethanol has a m.p. 222°–224° C.

EXAMPLE 35

3-p-Chlorobenzyl-2-(p-chlorophenyl)-6,7,8,9-tetrahydro-5H-thiazolo[3,2-a][1,3]diazocine hydrobromide When 2.0 g. of 3-p-chlorobenzyl-2-(p-chlorophenyl)-2,3,6,7,8,9-hexahydro-5H-thiazolo[3,2-a][1,3]diazocin-3-ol hydrobromide (Ex. 10) is immersed in an oil bath at 210° C. for 15 minutes, as described in Example 35, the desired compound is obtained.

EXAMPLE 36

6,7,8,9-Tetrahydro-3-p-methylbenzyl-2-p-tolyl-5H-thiazolo[3,2-a][1,3]-diazocine hydrobromide A 2.3 g. portion of 2,3,6,7,8,9-hexahydro-3p-methyl-benzyl-2-p-tolyl-5H-thiazolo[3,a-2][1,3]diazocin-3-ol hydrobromide (Ex. 15) is immersed in an oil bath at 200° C. for 20 minutes. The flask is removed and the contents are triturated with acetone and then filtered, giving the desired product, m.p. 190°–192° C.

EXAMPLE 37

3-p-Bromobenzyl-2-(p-bromophenyl)-6,7-dihydro-6,6-dimethyl-5H-thiazolo[3,2-a]pyrimidine hydrobromide When 3-p-bromobenzyl-2-(p-bromophenyl)-6,7-dihydro-6,6-dimethyl-5H-thiazolo[3,2-a]pyrimidine hydrobromide is reacted as described in Example 35 the desired product is obtained, m.p. 254°–257° C.

EXAMPLE 38

6,7,8,9-Tetrahydro-3-phenethyl-2-phenyl-5H-thiazolo-[3,2-a][1,3]diazocine hydrobromide A 2.0 g. portion of 2,3,6,7,8,9-hexahydro-3-phenethyl-2-phenyl-5H-thiazolo[3,2-a][1,3]diazocine-3-ol hydrobromide is placed in a flask and immersed in an oil bath at 210° C. for 15 minutes. The flask is removed and 10 ml. of acetone are added. The reaction mixture is cooled, giving the desired product.

We claim:

1. A compound selected from the group consisting of 2-(p-fluorophenyl)-3-(p-fluorobenzyl)-6,7-dihydro-5H-thiazolo[3,2-a]pyrimidine and the pharmacologically acceptable acid-addition salts thereof.

2. A compound selected from the group consisting of 2-(o-fluorophenyl)-3-(p-methoxyphenyl)-6,7-dihydro-5H-thiazolo[3,2-a]pyrimidine and the pharmacologically acceptable acid-addition salts thereof.

3. A compound selected from the group consisting of 2-phenyl-3-benzyl-6,6-dimethyl-6,7-dihydro-5H-thiazolo[3,2-a]pyrimidine and the pharmacologically acceptable acid-addition salts thereof.

4. A compound selected from the group consisting of 2-(p-fluorophenyl)-3-(p-fluorophenyl)-6,6-dimethyl-6,7-dihydro-5H-thiazolo[3,2-a]pyrimidine and the pharmacologically acceptable acid-addition salts thereof.

5. A compound selected from the group consisting of 2-(p-bromophenyl)-3-(p-bromobenzyl)-6,6-dimethyl-6,7-dihydro-5H-thiazolo[3,2-a]pyrimidine and the pharmacologically acceptable acid-addition salts thereof.

6. A compound selected from the group consisting of 2-(p-tolyl)-3-(p-methylbenzyl)-6,6-dimethyl-6,7-dihydro-5H-thiazolo[3,2-a]pyrimidine and the pharmacologically acceptable salts thereof.

7. A compound selected from the group consisting of 2-phenyl-3-(p-methoxyphenyl)-6,6-dimethyl-6,7-dihydro-5H-thiazolo[3,2-a]pyrimidine and the pharmacologically acceptable salts thereof.

* * * * *